(12) United States Patent
Horvath

(10) Patent No.: US 8,834,577 B2
(45) Date of Patent: Sep. 16, 2014

(54) THREE-DIMENSIONAL ARTIFICIAL CALLUS DISTRACTION

(75) Inventor: Domonkos Horvath, Jestetten (DE)

(73) Assignee: Celgen AG, Zug (CH)

( * ) Notice: Subject to any disclaimer, the term of this patent is extended or adjusted under 35 U.S.C. 154(b) by 817 days.

(21) Appl. No.: 12/444,367

(22) PCT Filed: Oct. 5, 2007

(86) PCT No.: PCT/EP2007/008648
§ 371 (c)(1),
(2), (4) Date: Apr. 3, 2009

(87) PCT Pub. No.: WO2008/043484
PCT Pub. Date: Apr. 17, 2008

(65) Prior Publication Data
US 2010/0049330 A1    Feb. 25, 2010

(30) Foreign Application Priority Data

Oct. 6, 2006    (DE) .......................... 10 2006 047 248

(51) Int. Cl.
| | | |
|---|---|---|
| *A61F 2/28* | (2006.01) |
| *D04H 3/16* | (2006.01) |
| *A61L 27/58* | (2006.01) |
| *A61L 27/18* | (2006.01) |
| *A61L 27/56* | (2006.01) |

(52) U.S. Cl.
CPC ................ *A61L 27/56* (2013.01); *A61L 27/58* (2013.01); *A61L 27/18* (2013.01)
USPC ........................................ 623/23.47; 264/115

(58) Field of Classification Search
None
See application file for complete search history.

(56) References Cited

U.S. PATENT DOCUMENTS

| | | | |
|---|---|---|---|
| 6,113,599 A * | 9/2000 | Landsberger | 606/60 |
| 6,280,191 B1 | 8/2001 | Gordon | |
| 6,350,284 B1 * | 2/2002 | Tormala et al. | 623/17.19 |
| 6,511,510 B1 | 1/2003 | de Bruijn et al. | |
| 2003/0057590 A1 | 3/2003 | Loher et al. | |
| 2003/0104339 A1 | 6/2003 | Fromovich et al. | |
| 2003/0133967 A1 * | 7/2003 | Ruszczak et al. | 424/443 |
| 2004/0254538 A1 * | 12/2004 | Murphy et al. | 604/181 |
| 2005/0074437 A1 | 4/2005 | Horvath | |
| 2005/0079159 A1 * | 4/2005 | Shastri et al. | 424/93.7 |
| 2005/0118236 A1 | 6/2005 | Qiu et al. | |
| 2005/0246021 A1 * | 11/2005 | Ringeisen et al. | 623/17.11 |
| 2007/0059827 A1 | 3/2007 | Horvath | |

FOREIGN PATENT DOCUMENTS

| | | | |
|---|---|---|---|
| CA | 2 281 608 A1 | 8/1998 | |
| DE | 197 06 667 A1 | 8/1998 | |
| DE | 10 2004 045 410 A1 | 3/2006 | |
| EP | 1 523 956 A | 4/2005 | |
| WO | WO-96/19336 | 6/1996 | |
| WO | WO-00/69361 A | 11/2000 | |
| WO | WO-01/91663 A | 12/2001 | |
| WO | WO-02/074356 A1 | 9/2002 | |
| WO | WO-03/048347 A | 6/2003 | |
| WO | WO03048347 A1 * | 6/2003 | ............... C12N 5/06 |
| WO | WO-2006/029621 A1 | 3/2006 | |
| WO | WO-2006/088866 A | 8/2006 | |

OTHER PUBLICATIONS

Sarkar, et al.: "Bone formation in a long bone defect model using a platelet-rich plasma-loaded collagen scaffold", Biomaterials, Elsevier Science Publishers BV., Barking, GB, vol. 27, No. 9, Mar. 2006, pp. 1817-1823, XP005204036, ISSN: 0142-9612.

Cano, et al.: "Osteogenic alveolar distraction: A review of the literature", Oral Surgery, Oral Medicine, Oral Pathology, Oral Radiology and Endodontics, Mosby-Year Book, St. Louis, MO, US, vol. 101, No. 1, Jan. 2006, pp. 11-28, XP005208890, ISSN: 1079-2104.

* cited by examiner

*Primary Examiner* — Robert A Wax
*Assistant Examiner* — Randeep Singh
(74) *Attorney, Agent, or Firm* — Harness, Dickey & Pierce, P.L.C.

(57) ABSTRACT

The present invention relates to devices for the regeneration of bone by three-dimensional callus distraction. The invention further relates to the use of such devices and to methods for three-dimensional callus distraction.

34 Claims, 1 Drawing Sheet

THREE-DIMENSIONAL ARTIFICIAL CALLUS DISTRACTION

CROSS-REFERENCE TO RELATED APPLICATIONS

Figure 1:
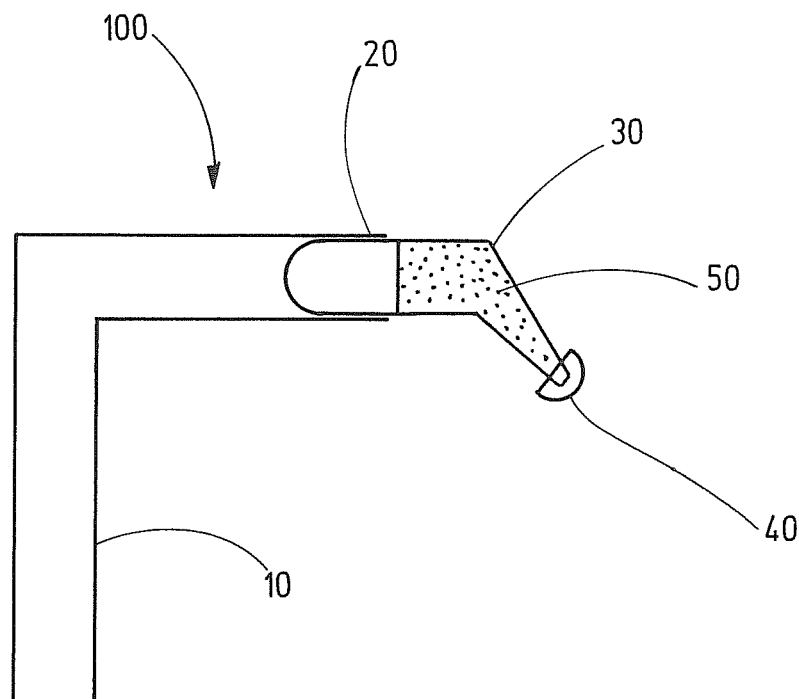

This application is a U.S. National Stage Application of International application No. PCt/EP2007/008648, filed Oct. 5, 2007. This application claims the benefit of German Application No. 10 2006 047 248.9, filed Oct. 6, 2006. The disclosure(s) of the above applications are incorporated herein by reference.

The present invention relates to a device for the regeneration of a bone, in particular by means of three-dimensional distraction, a method for three-dimensional callus distraction, and uses of said device.

At the present time, bone losses are generally filled using bone replacement materials, or autogenic or allogenic bone.

Examples of bone replacement materials include inorganic materials such as calcium phosphate, hydroxyapatite, or bioglass (which should be replaced by bone after a long absorption period. However, this procedure may be used only for minor defects; otherwise, there is the risk of infection due to insufficient vascularization. The absorption of inorganic materials is inadequate. Such bone materials, i.e., bone replacement materials, do not emit biomechanical pulses and therefore do not initiate active regeneration) and include also synthetically manufactured organic materials, such as polyesters, polyamino acids, polyanhydrides, polyorthoesters, polyphosphazenes, polylactides, or polyglycolides, or allogenic organic materials, for example of bovine origin. Material combinations of the various types of materials are also used as bone replacement composites. However, bone substance losses may also be compensated for using microvascular connected autogenic or allogenenically vascularized transplants. However, use of an allogenic bone replacement may trigger undesired immune reactions and transmit infection.

From a biological standpoint, the best replacement material for bone is an autologous spongiosa transplant. However, such transplants have limited availability and exhibit a high absorption rate after transplantation.

The materials and techniques used in the prior art frequently provide unsatisfactory bone quality, resulting, for example, in insecure anchoring of implant beds. In addition, frequently the bone replacement is insufficiently vascularized, thereby increasing the risk of infection. Furthermore, methods of the prior art often use growth factors which greatly increase the costs for the methods.

Instead of using a bone replacement, missing bone substance may sometimes be filled by bone regeneration. Segmented interruptions in the osseous continuity of long tubular bones may be treated in this manner by distraction osteogenesis.

Callus distraction has been known for over a hundred years. The most important biological stimulus for bone formation is mechanical stress. This releases piezoelectric forces which activate the osteoblasts and osteoclasts. Distraction osteogenesis induces new bone formation by triggering biological growth stimulation by means of slow separation of bone segments. This method achieves direction formation of woven bone by distraction. The defined tensile stress is essential for bone formation. When such a defined tensile stress is applied to bone fragments, the mesenchymal tissue exhibits an osteogenetic potential in the gap and at the contiguous fragment ends. When sufficient vascular potency is present, progressive distraction results in metaplasia of the organized hematoma, also referred to as blood coagulum, in a zone of longitudinally arranged fibrous tissue, which under optimal external and internal conditions may be directly converted to woven bone. A complication, however, is that the bone tissue requires highly complex control for regeneration.

WO 01/91663 describes a two-dimensionally oriented bone distraction using an artificial interface. For such distraction methods from the prior art, in many cases only vertical regeneration is possible, for example in the jaw region.

Thus, bone regeneration by distraction cannot be used for every type of bone defect. In addition, the devices used for distraction are complex, and distraction methods take a comparatively long time.

The technical object of the present invention is to provide a device which allows bone regeneration methods to be carried out which overcome the disadvantages of the prior art. A further technical object of the invention is to provide devices, use of same, and methods which allow simple and economical bone regeneration. A further technical object of the invention is the provision of devices, use of same, and methods which have improved quality and sufficient vascularization.

The technical object is achieved by the present invention in particular by providing devices, methods, and uses according to the claims.

The technical object is achieved by the present invention in particular by providing a three-dimensional framework for regenerating bone, comprising framework fibers composed of at least one framework material and interspaces enclosed by same, wherein the framework material is biocompatible, and expandable and/or shrinkable in a predefined and controlled manner as a function of an internal or external force effect, and the starting volume of the framework may be changed in a predefined and controlled manner as a function of the internal or external force effect.

Provision of the described three-dimensional framework allows the framework to be introduced into a bone defect, for example by surgical means. After introduction into the bone defect, according to the invention the volume of the introduced three-dimensional framework changes, for example increases or decreases in size, as the result of its design and composition, either directly and automatically without further action, or after introduction of an internal or external force. As a result, after introduction of the framework into the bone defect, osteogenic cells or cell aggregates which have migrated into the bone defect and adhered to the framework fibers are slowly exposed in a defined manner to stress, i.e., biomechanical stimulus, in particular when they are located at a distance from the framework for which distraction is effective, so that a callus precursor is produced in the entire defect all at once by distraction, and then only needs to ossify. This stimulus is advantageously achieved in essentially all cells at the same time. According to the invention, biomechanical stimuli may be transmitted directly to the osteoblasts without the need for fibroblasts. Thus, the distraction may act on the osteoblasts with comparatively small forces.

The framework according to the invention may advantageously be used in methods, preferably methods according to the invention, for bone regeneration, in particular for three-dimensional callus distraction.

The present teaching encompasses in particular devices and methods for bone regeneration, wherein preferably bone in the jaw region and/or periodontal region is to be regenerated.

In particular, for the present invention the term "bone regeneration" is also understood to mean the regeneration of bone defects, for example after cystectomy, tumor surgery, or trauma surgery, etc., regardless of the topography, and/or in particular also means the regeneration of minor bone defects, for example those caused by periodontitis.

In the context of the present invention, a "framework" is understood to mean a three-dimensional body. The framework comprises framework fibers composed of a framework material, as well as interspaces between the framework fibers. The framework fibers define the shape, border, and size of the framework, and are designed and configured in such a way that they result in a three-dimensional body (the framework) which defines a specified volume and which contains interspaces, for example pores, cavities, gaps, or hollow spaces, between the framework fibers. The volume of the framework may be changed, for example in a plastic or elastic manner, by a force effect, preferably without altering the structural identify of the framework, for example without removing or adding to the framework material. Such a framework may be present, for example, in the form of an interwoven mesh, porous cushion, sponge-like body, or matrix.

In the context of the present invention, "interspaces" of a three-dimensional framework according to the invention are understood to mean the volume of the framework which is not filled by a solid material, in particular by the framework fibers, and which is situated inside the overall volume of the framework. The interspaces may have various volumes, which, however, as a whole are smaller than the overall volume of the framework. The interspaces may have any shape. According to the invention the interspaces are preferably pores. The interspaces, for example pores, preferably have a diameter of 10 µm to 10 mm, preferably 10 µm to 1000 µm.

According to the invention the framework preferably contains interspaces, for example pores, having a maximum diameter of 100 µm. According to the invention, the framework preferably contains interspaces having a diameter of greater than 450 µm. According to the invention, the framework preferably contains interspaces having a diameter less than 100 µm as well as interspaces having a diameter greater than 450 µm. The framework material from which the framework is formed may use cells as a support structure. Pores having a pore size of less than 100 µm, for example, enable the growth of connective tissue. For pores with a pore size greater than 450 µm, blood vessels are able to grow into the framework and thereby vascularize the volume occupied by the framework.

According to the invention, at least a portion of the interspaces, particularly preferably the pores, preferably have a diameter of 0.5 µm to 5 µm. According to the invention, at least a portion of the interspaces, particularly preferably the pores, preferably have a diameter of 5 µm to 25 µm. According to the invention, at least a portion of the interspaces, particularly preferably the pores, preferably have a diameter of 100 µm to 1000 µm. According to the invention, at least a portion of the interspaces preferably have a diameter of 0.5 µm to 5 µm, a portion of the interspaces have a diameter of 5 µm to 25 µm, and a portion of the interspaces have a diameter of 100 µm to 1000 µm. According to the invention, preferably one-fourth, particularly preferably one-third, most particularly preferably one-half, of the interspaces, particularly preferably the pores, have a diameter of 0.5 µm to 5 µm. According to the invention, preferably one-fourth, particularly preferably one-third, most particularly preferably one-half, of the interspaces, particularly preferably the pores, have a diameter of 5 µm to 25 µm. According to the invention, preferably one-fourth, particularly preferably one-third, most particularly preferably one-half, of the interspaces, particularly preferably the pores, have a diameter of 100 µm to 1000 µm.

According to the invention, the diameter of the interspaces is preferably at least 450 µm and 5 mm maximum, particularly preferably at least 450 µm and 1000 µm maximum.

According to the invention, the framework preferably has open-pore guide structures which have a porosity that is particularly preferably 50% to 70%, in particular 60%, and which enable ingrowth of blood vessels.

According to the invention, the interspaces, for example pores, have a size, in particular a diameter, which allows transmission of extension stimuli to the cells present in the pores, of at least 0.5 µm, in particular 1 µm, more preferably 2 µm, most preferably 10 µm to especially 100 µm, particularly preferably 1000 µm, more particularly preferably 1 cm, most particularly preferably up to 10 cm. According to the invention, the extension stimuli are preferably transmitted with a distraction frequency of 1 mm/day maximum.

In the context of the present invention, the "volume" of a three-dimensional framework according to the invention is understood to mean the volume that is delimited by the framework fibers which define the outer surfaces of the framework. Thus, the volume of the framework is formed by the volume of the framework fibers and the volume of the interspaces enclosed by the framework fibers. The three-dimensional framework according to the invention is preferably present in the form of a starting volume, preferably the original volume, which is able to change to a different volume as the result of an internal or external force effect. A change in the volume means a change in the starting volume, specifically, either an increase in the starting volume, for example by expansion of the framework, or a decrease in the starting volume, for example by compression or shrinkage of the framework.

According to the invention, the framework material is expandable and/or shrinkable in a predefined and controlled manner as a function of an internal or preferably external force effect. The material may have plastic or elastic properties. These properties of the framework material allow the capacity of the framework provided according to the invention to reversibly or irreversibly change in a predefined and controlled manner.

In the context of the present invention, "in a predefined and controlled manner" is understood to mean a change in the starting volume, in particular an expansion or shrinkage, which occurs over a predetermined distance or a predetermined volume, and whose rate, i.e., the expansion rate, shrinkage rate, or rate of change in volume, is likewise predetermined, i.e., intentionally selected. According to the invention, a change in the volume may also be only a change in the shape of the volume. According to the invention, the point in time of the expansion, shrinkage, or start of the change in volume may also preferably be predetermined, i.e., intentionally selected.

According to the invention, the starting volume of the three-dimensional framework may preferably be changed by an externally supplied force. According to the invention, the force is preferably supplied using a tension cable or tension rod. According to the invention, the supplied force is preferably heat. According to the invention, the supplied force is preferably ultrasound. According to the invention, the force is preferably supplied by a magnet, and is therefore an electromagnetic force. According to the invention, the force may also preferably be a pressure exerted by, for example, a liquid or gas supplied from outside the framework.

According to the invention, the starting volume of the framework may preferably be changed by diffusion of a liquid, in particular interstitial liquid, into the framework system as the result of colloidal osmotic pressure. According to the invention, a necessary concentration gradient is preferably achieved by using dextran and/or hydroxylethyl starch.

In the context of the present invention, "expansion" is understood to mean an enlargement of the framework along at least one spatial axis, preferably along all three spatial axes. According to the invention, an expansion preferably results in an increase in volume of the framework.

In the context of the present invention, "shrinkage" is understood to mean a reduction in size of the framework along at least one spatial axis, preferably along all three spatial axes. According to the invention, the shrinkage of a framework preferably causes a reduction in the volume of the framework.

According to the invention, the shrinkage is preferably compression. Thus, according to the invention the framework material is compressible in a predefined and controlled manner as a function of an internal, or preferably external, force effect, so that in this manner the volume of the framework may also be changed. In the context of the present invention, "compression" is understood to mean shrinkage in which the framework is pressed together by an external force effect.

According to the invention, the starting volume may preferably be increased by filling the interspaces of the framework, particularly preferably the pores of the framework, with a liquid, particularly preferably a liquid containing biomolecules and/or cells, most preferably blood, preferably by a pressure exerted inwardly on the framework fibers by the inflowing liquid.

In the context of the present invention, "filling the interspaces" is understood to mean an at least partial inflow of a liquid into the interspaces. According to the invention, in the filling the interspaces are preferably filled for the most part, most preferably completely, with the liquid.

According to the invention, the framework preferably has at least one, preferably biodegradable, molded element. According to the invention the molded element is preferably a casing. According to the invention the molded element is preferably an interlacing, for example a thread. According to the invention the molded element is preferably an adhesive.

According to the invention the framework is preferably a molded element, as the result of which the framework is in an expanded starting volume. According to the invention the framework preferably has at least one molded element, as the result of which the framework is in a compressed starting volume. According to the invention the framework is preferably a molded element, as the result of which the framework is in an expanded or compressed starting volume, wherein the starting volume may be changed by removing the molded element, preferably mandatorily and automatically, in particular wherein the framework is present in a nonexpanded or uncompressed state.

According to the invention, the material of the molded element is preferably selected from the group comprising fibrin, collagen, at least one polysaccharide, and mixtures thereof. According to the invention, the biodegradable molded element is preferably fibrin or contains same. According to the invention, the biodegradable molded element is preferably collagen or contains same. According to the invention, the biodegradable molded element is preferably at least one polysaccharide or contains same.

According to the invention, the starting volume of the framework is preferably compressed or shrunk. According to the invention, the starting volume of the framework is preferably extended or expanded. According to the invention, the framework is kept in the particular shape in a compressed or expanded state by a biodegradable molded element.

According to the invention, the framework is preferably initially mechanically compressed or expanded after manufacture. According to the invention, the framework is preferably compressed by pressure or by drying and shrinkage. In one preferred design, the framework is then provided with the molded element in order to maintain the compressed or expanded starting volume until the start of the desired distraction.

According to the invention, the three-dimensional framework preferably has an elastic restoring force. Before the framework is used, the starting volume of the framework is changed, in particular compressed. In this state fixing is performed using a biodegradable molded element, for example an adhesive. When this biodegradable molded element, for example the adhesive, decomposes, the volume of the framework is changed by the elastic restoring force, thus allowing biomechanical stimuli to be triggered.

According to the invention, the three-dimensional framework preferably contains a spring made of biodegradable material. According to the invention, the spring, preferably in the compressed or stretched state, is fixed using a biodegradable molded element, for example a thread or adhesive. When the molded element disintegrates as the result of decomposition, i.e., absorption, the spring integrated into the framework causes the framework to change shape and thus emit biomechanical stimuli.

According to the invention, the absorption time for the molded element is shorter, in particular much shorter, than the absorption time for the framework.

According to the invention, the absorption time for the molded element is preferably at least one day, particularly preferably at least five days, most preferably at least seven days. According to the invention, the absorption time for the molded element is preferably twenty days maximum, more preferably fifteen days maximum, most preferably five days maximum.

According to the invention, the degradation kinetics of the framework and of the framework material are adapted to the time schedule of a volume distraction to be carried out using the framework according to the invention.

According to the invention, the starting volume of the three-dimensional framework is preferably changed at a predetermined rate. According to the invention, the maximum rate at which the starting volume of the framework is able to change is preferably great enough so that the cells adhering to the framework are distracted a maximum of 1.5 mm/day, particularly preferably 1.2 mm/day, in particular 1 mm/day, most preferably 0.9 mm/day.

In one preferred embodiment, the volume may be changed in a predefined and controlled manner at a rate at which expansion or shrinkage of a volume of 1000 $\mu m^3$ to 216,000 $\mu m^3$ in all three spatial coordinates is a maximum of 0.6 mm per day, particularly preferably a maximum of 0.577 mm per day, in particular a maximum of 0.55 mm per day, most preferably a maximum of 0.5 mm per day. In one preferred embodiment, the volume may be changed in a predefined and controlled manner at a rate at which expansion or shrinkage of a volume of 1000 $\mu m^3$ to 216,000 $\mu m^3$ in all three spatial coordinates is a minimum of 0.01 mm per day, particularly preferably a minimum of 0.1 mm per day, in particular a minimum of 0.2 mm per day, most preferably a minimum of 0.5 mm per day.

In one preferred embodiment, the volume may be changed in a predefined and controlled manner at a rate at which expansion or shrinkage of a section, between 10 $\mu m$ and 60 $\mu m$ long, of the body diagonal of the volume of the framework is a maximum of 0.6 mm per day, particularly preferably a maximum of 0.577 mm per day, in particular a maximum of 0.55 mm per day, most preferably a maximum of 0.5 mm per day. In one preferred embodiment, the volume may be changed in a predefined and controlled manner at a rate at which expansion or shrinkage of a section, between 10 μm and 60 μm long, of the body diagonal of the volume of the framework is a minimum of 0.01 mm per day, particularly preferably a minimum of 0.1 mm per day, in particular a minimum of 0.2 mm per day, most preferably a minimum of 0.5 mm per day.

According to the invention, the framework is preferably designed in such a way that the starting volume may be changed continuously. According to the invention, the framework is preferably designed in such a way that the changes in the starting volume may occur discontinuously.

According to the invention, the framework material, preferably the framework fibers, are not biogenic, and in particular contain no collagen, i.e., are collagen-free. According to the invention the framework material is preferably biogenic.

According to the invention the framework material is biocompatible.

According to the invention, the framework material preferably has at least one cell adhesive property, i.e., is able to bind cells, in particular osteoblasts, fibroblasts, and/or endothelial cells, preferably in a specific and selective manner. According to the invention, the cell adhesive property of the framework material is preferably determined by its surface characteristics.

According to the invention, the framework material and/or the framework are preferably biodegradable.

In the context of the present invention, "biodegradable" is understood to mean that the material may be degraded or absorbed by hydrolysis, polymer degradation, enzymatic decomposition, and/or dissociation of the material components, preferably in an organism, for example a human or animal organism. According to the invention, the degradation products of the framework material preferably have a molecular weight of 50,000 g/mol maximum, particularly preferably 40,000 g/mol maximum. Thus, they may be excreted in the normal manner.

According to the invention, the biodegradable framework material is preferably degraded in an organism within an absorption time of one year, particularly preferably within two months, in particular within one month, most preferably within two weeks.

According to the invention, the absorption preferably begins 6 weeks after the framework is introduced into an organism.

According to the invention, the absorption time for the framework material and/or the framework is particularly preferably at least 4 weeks, particularly preferably at least 8 weeks, in particular at least 16 weeks, most preferably at least 32 weeks. According to the invention, the absorption time for the framework material or the framework is preferably a maximum of 52 weeks, particularly preferably a maximum of 38 weeks, more preferably a maximum of 16 weeks, most preferably a maximum of 8 weeks.

According to the invention, the framework material is preferably composed of at least one polymer or contains same, and is preferably composed of spatially crosslinked polymers. Influx of water, blood, or serum results in formation of, for example, hydrogen bridges, sulfur bridges, or the like which cause spatial changes in the polymeric structure, resulting in a three-dimensional motion which generates a pulse for biomechanical stimulus transmission to the embedded cells.

According to the invention, the framework material preferably has good processing characteristics. According to the invention, the framework material and/or framework are sterilizable. According to the invention, the framework may preferably be adapted satisfactorily to the regeneration geometry. According to the invention, the framework material and/or framework preferably have good storage characteristics.

According to the invention, the framework material preferably contains a material selected from the group comprising polyglycolic acid, polylactic acid, poly(ε-caprolactone), poly(β-hydroxybutyrate), poly(p-dioxanone), a polyanhydride, or a mixture thereof, for example a mixture of polylactic acid and polyglycolic acid.

According to the invention, the framework material preferably contains copolymers, in particular composed of at least two of the previously named materials. According to the invention, the framework material preferably contains polymer mixtures.

According to the invention, the framework material is preferably composed of a material selected from the group comprising polyglycolic acid, polylactic acid, poly(ε-caprolactone), poly(β-hydroxybutyrate), poly(p-dioxanone), a polyanhydride, or a mixture thereof. According to the invention, the framework material preferably contains copolymers composed of at least two of the previously named materials.

According to the invention, the framework material is preferably composed of polylactic acid and polyglycolic acid. According to the invention, the polylactic acid and polyglycolic acid are preferably present as a copolymer.

According to the invention the framework material is preferably polyglycolic acid or contains same. According to the invention the framework material is preferably polylactic acid or contains same. According to the invention the framework material is preferably poly(ε-caprolactone) or contains same. According to the invention, the framework material is preferably poly(β-hydroxybutyrate) or contains same. According to the invention the framework material is preferably poly(p-dioxanone) or contains same. According to the invention the framework material is preferably at least one polyanhydride or contains same. According to the invention other suitable materials may also preferably be used.

According to the invention, the framework material is preferably composed of at least one polylactite and at least one polyglycolide.

According to the invention, copolymers having different physical and mechanical properties may preferably be produced by the combination and variation of the lactite and glycolide fractions and used as framework material.

According to the invention, the framework material preferably has specific rubber-elastic properties and has sufficient mechanical stability to overcome the tissue pressure present in the defect region of the bone. In particular, in one preferred embodiment the framework material and/or framework are capable of resisting an effective tissue pressure of up to 9.5 mm Hg in the tissue surrounding same.

According to the invention, the framework material is preferably anisotropic. In the context of the present invention, "anisotropy" is understood to mean the spatial variation in the macroscopic mechanical properties.

According to the invention, the surface of the framework material is preferably enlarged, in particular by providing contours. This enlargement not only increases the surface that is available to the cells, but also influences the organization of the cell growth.

According to the invention, the size and spatial distribution of the interspaces, in particular the pores, in the framework preferably determine the availability of the interspaces or pores to cells and exchange of nutrients. With increasing metabolic activity of the cells, the thickness of the blood vessels also increases in order to keep the metabolic paths by diffusion and osmosis between the active cells and the blood at a minimum. According to the invention, it is preferred to achieve the metabolism by providing suitable vascularized macroporosity. In a fine-pored framework the metabolism must overcome large distances, so that diffusion becomes the limiting factor.

According to the invention, the framework fibers preferably have a thickness of 5 to 3000 µm, preferably 50 µm to 3000 µm, preferably 60 µm to 2000 µm, in particular 100 µm to 1000 µm. According to the invention, the framework material, in particular the framework fibers, have a diameter of 5-50 µm.

According to the invention, the framework material, in particular the framework fibers, preferably have a thickness of 1-5 g/cm³. According to the invention, the framework material, in particular the framework fibers, preferably have rigidity and ductility, and a strength of 1000-8000 MPa. According to the invention the framework material, in particular the framework fibers, preferably have a modulus of elasticity of 50-500 GPa. According to the invention, the framework material, in particular the framework fibers, preferably have an elongation at break of 0.2-10%.

According to the invention, the framework preferably contains cells in the interspaces, in particular endothelial cells and/or osteoblasts and/or fibroblasts, before the introduction into a defect region of a bone.

According to the invention, the framework material is preferably composed of at least one fiber composite or contains same. According to the invention, the framework material is preferably composed of fibers of a fiber composite or contains same. According to the invention, the framework material is optionally encased by a thermoplastic matrix or is embedded in same. According to the invention, mechanical protection of the fibers under pressure and shear stress, strength under strain, and protection of the recipient tissue from the integrated fiber particles are thus provided. In particular, the invention optionally provides sealing of the three-dimensional fiber structure surface. The fibers may preferably be embedded in a matrix having, for example, a different layer thickness. According to the invention, in the framework material fibers of a fiber composite are preferably partly or completely embedded in a polymer matrix.

According to the invention the framework material is preferably coated. According to the invention the framework material is preferably coated using thin-layer technology. According to the invention the framework material is preferably coated using vacuum, plasma, or ion technology. Desired protein adsorption may be influenced in a targeted manner using a coating preferred according to the invention. In addition, hemocompatibility may be improved by coating with antithrombogenic surfaces. Cell adhesion to the framework material and influencing of cell growth of the adhered cells may be achieved in a controlled manner using a thin coating preferred according to the invention. The electrical properties of the surface of the framework material may be modified in a targeted manner using a coating preferred according to the invention.

According to the invention, the fibers of a fiber composite may preferably be coated to increase the cell adhesion. According to the invention the fibers are preferably coated with titanium. According to the invention the framework material is preferably coated with titanium. According to the invention the fibers are preferably coated with titanium oxide. According to the invention the framework material is preferably coated with titanium oxide. According to the invention the fibers are preferably coated with sodium alginate. According to the invention the framework material is preferably coated with sodium alginate.

According to the invention the fibers are preferably coated with a hydrogel. According to the invention the framework material is preferably coated with a hydrogel. According to the invention, the hydrogel coating may preferably be used so that the volume of the framework does not immediately change after the framework is introduced into a bone defect, or does not change until a later point in time, particularly preferably after one week.

To allow the most effective use possible of the framework according to the invention, osteoblasts must be able to bind well to the framework fibers. As the result of improved adhesion between the framework and the osteoblasts, when a framework according to the invention is used, in particular in a method according to the invention, more osteoblasts are activated by the framework by means of one or more biomechanical pulses. For this reason, the framework material or the coating for the framework material is preferably designed according to the invention in such a way that optimum osteoblast binding to the framework can take place. According to the invention, the adhesion binding of the osteoblasts to the framework is preferably so strong that the binding is maintained during a portion of the volumetric expansion, particularly preferably during the entire volumetric expansion, of the framework, in particular when the framework is used in a method according to the invention.

According to the invention the fibers are preferably smooth. According to the invention the framework material is preferably smooth. According to the invention the coating for the framework material is preferably smooth. According to the invention the fibers are preferably rough. According to the invention the framework material is preferably rough. According to the invention the coating for the framework material is preferably rough. A large surface is available for binding of the osteoblasts by use of a preferred rough surface according to the invention.

According to the invention the fibers are preferably coated with hydroxyapatite. According to the invention the framework material is preferably coated with hydroxyapatite. A coating with hydroxyapatite preferred according to the invention allows binding-promoting adsorption of proteins.

According to the invention the fibers are preferably coated with a hydrogel. According to the invention the framework material is preferably coated with a hydrogel. According to the invention the hydrogel layer is thin.

According to the invention the fibers are preferably coated with at least one protein. According to the invention the framework material is preferably coated with at least one protein. According to the invention the at least one protein contains the amino acid sequence Arg-Gly-Asp, i.e., RGD. According to the invention the fibers are preferably coated with at least one peptide. According to the invention the framework material is preferably coated with at least one peptide. According to the invention the at least one peptide is preferably a peptide which initiates the cell adhesion. According to the invention the at least one peptide is preferably an RGD peptide. According to the invention the at least one peptide is preferably synthetically produced. According to the invention the at least one peptide preferably contains the amino acid sequence Arg-Gly-Asp, i.e., RGD. According to the invention the at least one peptide preferably comprises the amino acid sequence Arg-Gly-Asp, i.e., RGD.

According to the invention the fibers are preferably coated with star-shaped polyethylene glycol polymers (star PEG).

According to the invention the framework material is preferably coated with star-shaped polyethylene glycol polymers (star PEG).

According to the invention, the at least one protein is preferably bound to the polyethylene glycol polymer coating, particularly preferably covalently bound. According to the invention, the at least one peptide is preferably bound to the polyethylene glycol polymer coating, particularly preferably covalently bound.

The adhesion of osteoblasts is a receptor-mediated contact between the molecules of the extracellular matrix and the actin fibers of the cytoskeleton. This region is also referred to as the focal contact zone. Molecules which provide for binding as well as molecules which are responsible for signal transduction are present in the focal contacts. Formation of the focal adhesion is caused primarily by integrins. The integrins differ from other cell surface receptors by virtue of their bioaffinity. Adhesion proteins in the form of an ultrathin coating on the framework material facilitate the adhesion binding of osteoblasts to the framework according to the invention. Fibronectin is an extracellular adhesion protein having several specific binding sites for receptors, and is therefore used for binding the osteoblasts to the extracellular matrix. Fibronectin is a large glycoprotein, which as a dimer is composed of two essentially identical subunits. Fibronectin is composed of approximately 90 amino acids. The cell-binding site of fibronectin has been identified as the tripeptide sequence Arg-Gly-Asp (RGD).

The properties of the fiber composites, with or without a matrix, may preferably be specified according to the invention by the fiber volumetric capacity and by the orientation of the fibers in the fiber architecture. In this manner the strength and the modulus of elasticity of the framework according to the invention may also preferably be specified according to the invention.

If the framework is preferably according to the invention composed of fibers of a fiber composite, or if the framework contains such fibers, the framework according to the invention is preferably designed in such a way that a stress is able to occur in the fiber direction or perpendicular to the fiber direction. However, according to the invention the framework may also be designed in such a way that stresses are able to occur in various directions in relation to the fiber direction. According to the invention, for a stress perpendicular to the fiber direction the fibers are preferably arranged in series. When a matrix is preferably used between the fibers according to the invention, this matrix is thereby subjected to greater stress.

According to the invention, the three-dimensional framework is composed of a fiber composite made of continuous fibers, or contains same.

According to the invention, a framework is preferably composed of a fiber composite made of differently oriented layers. According to the invention, the layer sequence of the fibers may preferably be symmetrical to the center plane of the framework, or may be configured randomly or in intermediate stages.

According to the invention, fibers of a fiber composite preferably represent the primary load-bearing element of a framework having a thermoplastic matrix. Because of their higher modulus of elasticity and higher strength, the fibers largely determine the mechanical properties of the composite.

According to the invention, the framework preferably contains a fiber architecture in the form of a nonwoven fabric, a two-dimensional framework, a multiaxial framework, and/or a three-dimensional interwoven mesh.

According to the invention, a unidirectional woven fabric is preferably used as the fiber architecture for the framework.

According to the invention, the fiber architecture of the framework is preferably a biaxial woven fabric. According to the invention, the fiber architecture of the framework is preferably a knitted fabric. According to the invention, the fiber architecture of the framework is preferably a multiaxial, multilayered knitted fabric.

According to the invention, the framework is preferably characterized by its biofunctionality. The physical, mechanical, and/or biological properties in conjunction with the time-related biomechanical stimulus emission are important for biofunctionality.

The selection of specific preferred architectures according to the invention, in particular knitting techniques, for the design of the framework composed of the framework material allows the density, distribution, and orientation of the framework material to be controlled, and is an effective means for designing structures which provide controllability of the mechanical behavior and the growth of cells into the framework.

According to the invention, the surface of the framework material is preferably chemically modified. According to the invention, the surface of the framework material is preferably chemically modified by reactive molecules or groups of molecules. According to the invention, the molecules or groups of molecules by means of which the surface of the framework material is chemically modified are preferably able to react with anchor proteins of the extracellular matrix of cells. According to the invention the surface of the framework material is preferably hydrophilic. Hydrophilic surfaces allow better adhesion for cells than do hydrophobic surfaces. The surfaces of each framework correspond to the polarizability of the framework.

The invention further relates to a three-dimensional framework which for a specified period of time is able to pulse or vibrate, for example as the result of excitation by a magnetic field or ultrasound, thus allowing emission of biomechanical stimulus pulses for osteogenic cells.

According to the invention, the structural elements of the framework may preferably be configured according to a stochastic, fractal, or periodic principle.

According to the invention the framework is preferably composed of substructures and simple subsystems. According to the invention, the complexity of the framework may preferably be increased by a hierarchical sequence of structural elements over several stages in which the smallest functioning unit is combined into groups, which in turn are combined with additional groups having a different functionality to produce larger units.

According to the invention, a plurality of frameworks may preferably also be present in the form of a granulate. The base units of the granulate, i.e., the individual frameworks, have an identical or similar design, but are not combined into a superstructure. According to the invention the individual granule particles, i.e., the individual frameworks, are preferably fixed to one another using a biodegradable adhesive, and in this manner may be incorporated into the defect.

The invention further relates to the use of at least one three-dimensional framework according to the invention described within the scope of the present teaching, in one preferred embodiment optionally containing a spring, for producing a bone regeneration kit. The invention further relates to the use of a granulate according to the invention, composed of frameworks for producing a bone regeneration kit. According to the invention, said kits preferably contain at least one surgical instrument, particularly preferably at least one applicator, for example a syringe, and a capsule for accommodating the framework, for example the framework in granulate form. According to the invention, the kit preferably contains a user's manual. According to the invention, the kit preferably contains packaging, particularly preferably packaging which allows sterile storage of the framework. According to the invention, the kit preferably contains an adhesive, in particular an adhesive for fixing the framework in a bone defect.

In a further embodiment of the invention, the invention relates to the use of a three-dimensional framework according to the invention for producing a bone regeneration kit, the kit also having a molded element of the above-referenced type, for example a casing, an adhesive, or an interlacing.

The invention further relates to the use of a biocompatible framework material which is expandable and/or shrinkable in a predefined and controlled manner as a function of an internal or external force effect, and which has a cell adhesive property for producing a three-dimensional framework comprising a framework material and interspaces enclosed by same for regeneration of a bone, wherein the three-dimensional framework may be introduced into a defect region of a bone.

The invention further relates to provision of a method for producing a three-dimensional framework for regeneration of a bone, wherein, using a biocompatible framework material which is expandable and/or shrinkable in a predefined and controlled manner as a function of an internal or external force effect, and which has a cell adhesive property, a framework is formed which is able to change its starting volume in a predefined and controlled manner as a function of the internal or external force effect.

The invention relates in particular to a method for producing a three-dimensional framework according to the invention, wherein framework fibers composed of at least one nonbiogenic framework material are formed into a framework in an extrusion process, the framework material being biocompatible, and being expandable and/or shrinkable in a predefined and controlled manner as a function of a force effect, and having a cell adhesive property.

According to the invention, the interspaces which are enclosed by the framework material are produced by leaching out salts from salt-polymer mixtures.

According to the invention, for production of the framework fibers felts made of polymer fibers may preferably be stabilized by gluing the fibers in the framework. According to the invention the framework material, in particular a polymer, may be foamed using thermally activated foaming agents or by pressurized expansion. According to the invention, the interspaces which are enclosed by the framework material are preferably produced using a sol-gel process.

The invention achieves its underlying technical object, and therefore further relates to provision of a method for regeneration of a bone, wherein at least one above-referenced three-dimensional framework, in particular comprising a framework material forming framework fibers and interspaces enclosed by the framework fibers, is introduced into a defect region of a bone, wherein the framework material is biocompatible, and is expandable and/or shrinkable in a predefined and controlled manner as a function of a force effect, and has a cell adhesive property, in particular for osteoblasts, fibroblasts, and/or endothelial cells, and wherein the framework is subjected to an internal or external force effect, and the starting volume of the framework changes in a predefined and controlled manner as a function of the force effect.

Accordingly, within the scope of the method according to the invention for bone regeneration, in one preferred embodiment a three-dimensional framework is introduced into a defect region of a bone. In this defect region the framework is enclosed by a blood clot; i.e., the surfaces of the framework in the framework interior as well as on the external surfaces make contact with the autologous cells contained in the blood clot. According to the invention the interspaces enclosed by the framework material are preferably filled at least partially, particularly preferably for the most part, in particular completely, by the blood clot. Since the framework has a three-dimensional design, the framework surface comes into contact with the autologous cells contained in the blood clot in the entire space that is filled by the framework. After the framework has been introduced into the defect region of a bone, a change in volume, i.e., in particular a decrease or increase in volume, of the framework is triggered, for example by the action of an external or internal force, for example also by removing a molded element. This results in the desired biomechanical stimulation of the embedded osteogenic cells, and thus results in distraction and therefore bone regeneration. According to the invention, the force effect preferably occurs within the body, in particular within the bone defect. According to the invention, the force effect preferably occurs on a molded element, for example an adhesive or a thread, which fixes the three-dimensional framework in a compressed and/or expanded state. According to the invention, the molded element, for example the adhesives or threads, is preferably destroyed, in particular biodegraded, by an external force effect. As the result of destruction of the molded element, for example the adhesive or thread, the three-dimensional framework is able to return to the unexpanded and/or uncompressed state, thereby changing the volume of the three-dimensional framework.

According to the invention, the volume of the framework is changed as a function of an external force effect. According to the invention, the external force effect preferably occurs outside the body. According to the invention, the external force effect preferably occurs via tension cables and/or rods. According to the invention, the external force effect preferably occurs by means of at least one magnet. According to the invention, the force effect preferably occurs by means of ultrasound.

According to the invention, the change in volume of the framework may lie in various ranges. The volume change is preferably approximately 10% of the longitudinal expansion of the embedded cells or cell groups.

For a pore size of 100 µm, individual cells, for example osteoblasts, are embedded in the framework. For a cell size of 10 µm, the daily spatial extension distance is preferably at least 1 µm (lower limit), specifically, approximately 10% of the cell size.

For a pore size of 100-1000 µm according to the invention, mixed cell colonies are preferably embedded in the pores, for example osteoblasts, fibroblasts, etc. A daily spatial extension distance of 10 to 100 µm is then preferred, likewise approximately 10%, in this case of the colony size.

For a pore size of 1000 µm-10 mm according to the invention, adherent tissue cells of connective tissue, callus, callus precursors, or others are preferably embedded. The daily increase in spatial extension is preferably 0.3-1 mm (upper limit), likewise approximately 10%, in this case of the tissue size.

According to the invention, the change in the extension distance is at least 0.5 µm, particularly preferably at least 1 µm, more preferably at least 10 µm, even more preferably at least 100 µm, very preferably at least 1000 µm, very particularly preferably at least 10 mm, most preferably at least 100 mm.

According to the invention, the change in the extension distance is preferably 100 mm maximum, particularly preferably 10 mm maximum, more preferably 1000 μm maximum, even more preferably at least 100 μm, very preferably 10 μm maximum, very particularly preferably 1 μm maximum, most preferably 0.5 μm maximum.

According to the invention, the rate of change of the volume is at least great enough that cells adhering to the framework are distracted at least 1 μm/day. According to the invention, the maximum rate of change of the volume is great enough that cells adhering to the framework, i.e., osteogenic, callus-producing tissue, is distracted a maximum of 1 mm/day. A more rapid distraction rate than 1 mm/day results in differentiation of connective tissue instead of bone. As a result of the change in volume, the framework transmits to the cells contained in the blood clot and adhered to the framework material, also in the interior of the framework, biomechanical stimuli which trigger the body's own regenerative forces, thereby forming new autologous bone material. This new bone material does not differ from the original bone material surrounding the defect. The change in volume of the three-dimensional framework results in biomechanical stimulus transmission throughout the entire space occupied by the framework, so that a biomechanical stimulus is transmitted to a much larger number of cells than for distraction osteogenesis from the prior art. According to the invention, the biomechanical stimulus is preferably transmitted from the framework directly to osteoblasts.

For a distraction according to the invention, the biomechanical stimuli according to the invention are transmitted not only directly to osteoblasts adhering to the framework, but also indirectly via fibroblasts. According to the invention, fibroblasts adhering to the framework preferably further transmit the distraction stimulus to osteoblasts in a metered manner. Without being bound to theoretical aspects, after completion of the distraction the fibroblasts in the so-called "null zone" also become osteoblasts and likewise form bone. For a decreasing distraction rate, the number of fibroblasts preceding the osteoblasts changes.

In contrast, distraction osteogenesis from the prior art transmits biomechanical stimuli via a two-dimensional interface composed of bone or another material only to cells which directly contact this two-dimensional interface.

Thus, the invention provides a method in which a three-dimensional framework is introduced into a bone defect, and the three-dimensional framework in the bone defect changes in volume. As a result of the change in volume, biomechanical stimuli are transmitted to cells, in particular osteoblasts, present in the volume of the three-dimensional framework, thereby stimulating the cells to form bone. The three-dimensional framework thus transmits biomechanical stimuli for utilization of the body's own regenerative forces.

The method according to the invention is therefore a three-dimensional distraction. In the context of the present invention, "three-dimensional distraction" is understood to mean distractive bone regeneration in which the biomechanical stimuli are transmitted to a bone fragment not only at the interface, i.e., in two dimensions, but also throughout a given volume, i.e., in three dimensions.

The method according to the invention uses the body's own healing mechanisms as a bioreactor. Thus, the bone formation occurs under natural conditions, so that the necessary aspects such as growth factors, hormones, and cell composition are implicitly taken into account. In this manner the method according to the invention overcomes problems which may arise as a result of the highly complex control for bone regeneration, as well as the problems of a slow and complicated bone regeneration process using distraction methods from the prior art.

According to the invention, the bone defect is preferably revivified before introduction of the framework. According to the invention, in the method according to the invention before introduction of the framework into a bone defect this defect is preferably surgically revivified, and in particular bleeding is induced. A blood clot forms in the defect as a result of the surgical revivification and the induced bleeding.

After the surgical revivification of the bone defect, according to the invention a framework, in particular a framework according to the invention, is preferably introduced into the bone defect. The framework material of the introduced framework is enclosed, in particular completely enclosed, by the blood clot which forms; i.e., in particular the interspaces, particularly preferably the pores, of the framework are filled, particularly preferably completely, with the blood clot.

According to the invention, the framework preferably changes in volume after a defined point in time. According to the invention, the framework preferably changes in volume after one day. According to the invention, the framework preferably changes in volume after one week. As a result of the change in volume, according to the invention preferably also the shape and/or size of the interspaces, in particular pores, in the framework change, so that the framework simultaneously or successively emits in all directions, i.e., in three dimensions, stimuli to the cells adhering to the framework which are distributed over the space. As a result the blood clot does not shrink, but instead enlarges corresponding to the increase in volume of the framework. The cells activated by the framework may be converted to proliferating osteoblasts which produce the extracellular matrix, and a callus may be formed which subsequently ossifies. When the framework according to the invention is preferably biodegradable, the framework is subsequently absorbed and/or metabolized. Thus, the bone defect may be filled with bone tissue which according to the invention is preferably produced by the described biomechanical stimuli from the framework. According to the invention, artificially introduced bone replacement materials, growth factors, and other substances next to the framework may preferably be dispensed with. According to the invention, the newly formed bone material preferably does not differ, either histologically or in its biological or medical value, from the original bone which surrounds it.

Since the framework according to the invention is preferably biodegradable, the space resulting from the degradation of the framework may be used for the extracellular matrix. According to the invention, the degradation of the framework may preferably be adjusted in such a way that after a few weeks the framework degrades after it has emitted the biomechanical stimuli, and the resulting space is occupied by the extracellular matrix.

According to the invention, within the scope of the method according to the invention a framework is preferably used whose framework material has cell adhesive properties. The surface of the framework material particularly preferably has cell adhesive properties. The surface of the framework material in the framework plays an important role in the growth of cells from the blood clot. An adhesion of the cells to the framework material preferred according to the invention may be influenced by the surface chemistry, surface physics, and surface topography of the framework material. According to the invention the surface of the framework material is preferably hydrophilic. For the ingrowing cells, the interaction between the negatively charged cell membrane and the electrical properties of the framework material surface is preferred according to the invention.

According to the invention, a biodegradable framework is preferably introduced into the defect region of a bone. According to the invention, the absorption of the framework material preferably begins 6 weeks after the framework is introduced into a defect region of a bone.

In another embodiment the invention relates to a further method according to the invention for bone regeneration, in particular a further three-dimensional distraction method, in particular an above-referenced three-dimensional framework being introduced into a defect region of a bone and moved at that location. In this defect region the framework is enclosed by a blood clot; i.e., the surfaces of the framework contact the autologous cells contained in the blood clot. According to the invention the interspaces enclosed by the framework material are preferably filled at least partially, particularly preferably for the most part, in particular completely, by the blood clot. Since the framework has a three-dimensional structure, the framework surface is able to come into contact with the autologous cells contained in the blood clot in the entire space that is filled by the framework. After the framework has been introduced into the defect region of a bone the framework is moved within the bone defect. The motion takes place in a controlled and directed manner, i.e., in a predefined direction at a defined rate. As a result of the motion, the framework transmits to the cells contained in the blood clot and adhered to the framework material biomechanical stimuli which trigger the body's own regenerative forces, thus causing new autologous bone material to be formed. This new bone material does not differ from the original bone material surrounding the defect. The motion of the three-dimensional framework results in biomechanical stimulus transmission throughout the entire space defined by the framework, so that a biomechanical stimulus is transmitted to a much larger number of cells than for distraction osteogenesis from the prior art.

Thus, the invention provides a method in which a three-dimensional framework is introduced into a bone defect, and the three-dimensional framework is moved in the bone defect. In this embodiment a change in volume of the framework is not necessary, but is possible. As a result of the motion, biomechanical stimuli are transmitted to cells, in particular osteoblasts, which are present in the volume of the three-dimensional framework, and the cells are thereby stimulated to form bone. The three-dimensional framework thus transmits biomechanical stimuli for utilization of the body's own regenerative forces.

According to the invention, a method for regeneration of a bone is preferred wherein at least one three-dimensional framework, comprising a framework material forming the framework fibers and interspaces enclosed by the framework fibers, is introduced into a defect region of a bone, the framework material being biocompatible and having a cell adhesive property, and after introduction into the defect region the framework being moved in the bone defect in a predefined and controlled manner as a function of a force effect.

According to the invention, the framework is preferably moved at a rate of at least 1 μm/day and/or 1.5 mm per day maximum, particularly preferably 1 mm per day maximum. According to the invention the motion is carried out continuously or discontinuously.

According to the invention, a biodegradable framework is preferably introduced into the defect region of a bone. According to the invention, the absorption preferably begins 6 weeks after the framework is introduced into a defect region of a bone.

According to the invention, the three-dimensional framework used is preferably a three-dimensional framework according to the invention. According to the invention, in the method the volume of the three-dimensional framework preferably does not change during the motion of the framework.

According to the invention, the method according to the invention for stimulus transmission via a change in volume of a three-dimensional framework may preferably be combined with the method according to the invention for stimulus transmission via motion of a three-dimensional framework. The disclosed preferred features of the method according to the invention for stimulus transmission via a change in volume are in particular also preferred features of the method according to the invention for stimulus transmission via motion.

According to the invention, the motion of the three-dimensional framework may preferably be carried out by means of at least one externally supplied force. According to the invention, the force is preferably introduced using a tension cable or tension rod. According to the invention the introduced force is preferably ultrasound. According to the invention the force is preferably supplied by a magnet.

The invention further relates to the use of a biocompatible framework material which is expandable and/or shrinkable in a predefined and controlled manner as a function of an internal or external force effect, and has a cell adhesive property for producing a three-dimensional framework, comprising framework fibers made of the framework material and interspaces enclosed by these framework fibers, for regeneration of a bone, wherein the three-dimensional framework is or may be introduced into a defect region of a bone.

Further advantageous embodiments of the invention result from the subclaims. The invention is explained in greater detail below with reference to the following exemplary embodiment and the accompanying figures.

FIG. 1 shows a kit comprising three-dimensional frameworks in an applicator in the form of a syringe; and FIG. 2 schematically shows a three-dimensional framework which is introduced into a bone defect, before and after a change in volume.

EXAMPLE

FIG. 1 shows a kit 100 which contains an applicator syringe 10 made of sterilizable metal, on the open end 20 of which a disposable capsule 30, made of plastic, for example, is attached. The outwardly facing side of the disposable capsule 30 is provided with a protective cap 40. The disposable capsule 30 contains a plurality of three-dimensional frameworks 50 in the form of a granulate. The three-dimensional frameworks are injected via the syringe into a bone defect (not illustrated), for example in the jaw region.

The kit 100 according to the invention is used to inject the granulate composed of the three-dimensional frameworks 50 into a bone defect. After introduction into the bone defect, as a result of the structure and composition of the framework material according to the invention the volume of the three-dimensional framework 50 changes, and for regeneration of the bone distracts the bone cells which in the meantime have become embedded in the framework.

Figure 2A:
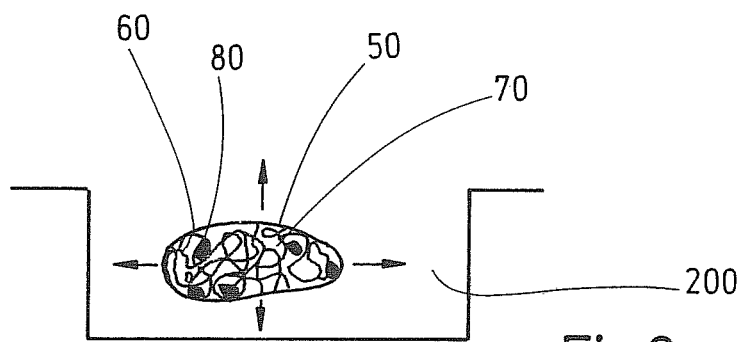
Figure 2B:
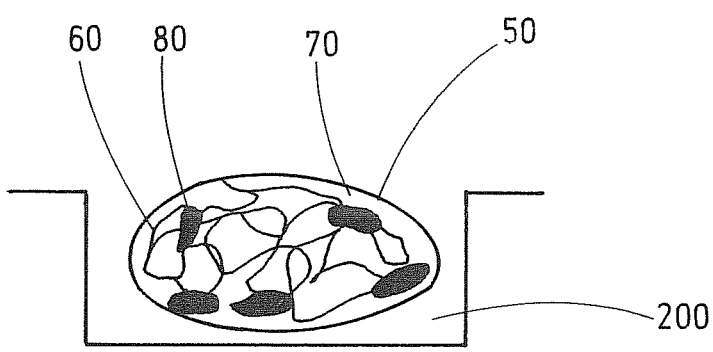

FIG. 2a shows an absorbable framework 50, made of an elastic polymer, in a bone defect 200, specifically, immediately after this framework 50 has been introduced into the bone defect 200, for example by use of a kit 100. The framework 50 is composed of framework fibers 60 and interspaces 70. Several osteogenic cells, for example osteoblasts 80, are already embedded in the interspaces 70 and adhere to the framework fibers 60. After being manufactured and before being introduced into the defect 200, the framework 50 made of the elastic polymer has been mechanically compressed, and then fixed in this compressed form by immersion into a bath of a bioabsorbable crosslinking solution, for example another polymer. After being introduced into the defect 200 the bioabsorbable crosslinking solution is continuously absorbed in a predefined manner, as the result of which, as schematically illustrated by the arrows in FIG. 2a, the framework 50 spatially expands, i.e., enlarges, in all three dimensions, so that, as shown in FIG. 2b, a framework 50 with increased volume results as soon as the bioabsorbable crosslinking solution has been completely absorbed. The increase in volume results in distraction of the adhered cells 80 embedded in the framework 50.

The invention claimed is:

1. A three-dimensional framework for the regeneration of a defect region of a bone, comprising framework fibers composed of at least one framework material and interspaces enclosed by same, wherein the framework fibers have a thickness of 50 μm to 3000 μm, wherein the framework material is biocompatible, has a volume that is expandable and/or shrinkable in a predefined and controlled manner as a function of a force effect and has a cell adhesive property, and wherein the framework has an elastic restoring force which allows a starting volume of the framework to be changed in a predefined and controlled manner as a function of the force effect such that the starting volume is changed at a rate such that the cell adhesive property is operable to distract a cell at a rate less than or equal to 1.5 millimeters per day by filling the interspaces with a liquid or by removing a molded element from the framework;
wherein the framework is collagen-free.

2. The framework according to claim 1, wherein the interspaces of the framework are filled with a liquid and the starting volume is resultantly enlarged.

3. The framework according to claim 1, wherein the framework includes the molded element and the molded element provides an expanded or compressed starting volume for the framework, and wherein the starting volume is changed by removing the molded element from the framework.

4. The framework according to claim 3, wherein the material of the molded element is selected from a group consisting of fibrin, collagen, at least one polysaccharide, and mixtures thereof.

5. The framework according to claim 1, wherein the framework material contains a material selected from the group consisting of polyglycolic acid, polylactic acid, poly(c-caprolactone), poly(β-hydroxybutyrate), poly(p-dioxanone), a polyanhydride, and mixtures thereof.

6. The framework according to claim 1, wherein the framework material is composed of a material selected from the group consisting of polyglycolic acid, polylactic acid, poly (c-caprolactone), poly(β-hydroxybutyrate), poly(p-dioxanone), a polyanhydride, and mixtures thereof.

7. The framework according to claim 1, wherein the framework material is composed of polylactic acid and polyglycolic acid.

8. The framework according to claim 1, wherein the framework material is anisotropic.

9. The framework according to claim 1, wherein the framework material contains fibers of a fiber composite.

10. The framework according to claim 1, wherein the framework fibers of the framework material have a thickness of 60 μm to 2000 μm.

11. The framework according to claim 1, wherein the interspaces are designed as pores.

12. The framework according to claim 1, wherein the interspaces have a diameter of 0.5 μm to 5 μm.

13. The framework according to claim 1, wherein the interspaces have a diameter of 5 μm to 25 μm.

14. The framework according to claim 1, wherein the interspaces have a diameter of 100 μm to 1000 μm.

15. The framework according to claim 1, wherein a portion of the interspaces have a diameter of 0.5 μm to 5 μm, a portion of the interspaces have a diameter of 5 μm to 25 μm, and a portion of the interspaces have a diameter of 100 μm to 1000 μm.

16. The framework according to claim 1, wherein the framework material is biodegradable.

17. A method for producing a three-dimensional framework according to claim 1, wherein framework fibers composed of at least one nonbiogenic framework material are formed into a framework in an extrusion process, wherein the framework material is biocompatible and is expandable and/ or shrinkable in a predefined and controlled manner as a function of a force effect, and has a cell adhesive property.

18. The framework according to claim 2, wherein the liquid is selected from a group consisting of biomolecules and combinations thereof.

19. The framework according to claim 2, wherein the liquid is blood.

20. The framework according to claim 3, wherein the molded element is selected from a group consisting of a casing, interlacing and adhesive.

21. The framework of claim 1, wherein the framework is made of an elastomeric polymer that is fixed into a compressed form and adapted to elastically expand through absorption of a liquid.

22. The framework of claim 21, where the framework has a modulus of elasticity of between 50-500 GPa and is adapted to resist an effective tissue pressure of up to 9.5 mm Hg from a surrounding tissue upon implantation.

23. The framework of claim 1, wherein the starting volume of the framework material is changed at a rate such that the cell adhesive property is operable to distract a cell at a rate greater than or equal to 1 micrometer per day.

24. The framework of claim 1, wherein a surface of the framework material is contoured and includes the cell adhesive property.

25. The framework of claim 1, further comprising layers of framework fibers, wherein the layers of framework fibers are symmetrical in relation to a plane intersecting the center of the three-dimensional framework.

26. A method for the regeneration of a bone comprising:
introducing at least one three-dimensional framework having a framework material forming framework fibers and having interspaces enclosed by the framework fibers into a defect region of a bone, wherein the framework fibers have a thickness of 50 μm to 3000 μm, wherein the framework material is biocompatible, and has a volume that is expandable and/or shrinkable in a predefined and controlled manner as a function of a force effect, and has a cell adhesive property; and
subjecting the framework is a force effect such that a starting volume of the framework changes in a predefined and controlled manner as a function of the force effect at a rate such that the cell adhesive property is operable to distract a cell at a rate less than or equal to 1.5 millimeters per day;
wherein the framework is collagen-free.

27. The method according to claim 26, wherein the framework is a framework according to claim 25.

28. The method according to claim 26, comprising revivifying the bone defect before introduction of the framework.

29. A method for the regeneration of a bone comprising:
introducing at least one three-dimensional framework having a framework material forming framework fibers and having interspaces enclosed by the framework fibers into a defect region of a bone, wherein the framework fibers have a thickness of 50 μm to 3000 μm, wherein the framework material is biocompatible and has a cell adhesive property; and moving the framework in a predefined and controlled manner as a function of a force effect after introduction into the defect region to perform three-dimensional callus-distraction;

wherein moving the framework is collagen-free and includes filling the interspaces with a liquid to increase a starting volume of the framework at a rate such that the cell adhesive property is operable to distract a cell at a rate less than or equal to 1.5 millimeters per day.

30. The framework of claim 26, wherein the framework material encloses interspaces and wherein the method further includes filling the interspaces with a liquid to increase a starting volume of the framework.

31. The framework of claim 26, wherein the framework includes a molded element and the method further includes expanding or compressing a starting volume of the framework with the molded element and changing the starting volume by removing the molded element from the framework.

32. The method for the regeneration of a bone of claim 26, wherein the framework is made of an elastomeric polymer and wherein the method further comprises fixing the framework into a compressed form prior to implantation and elastically expanding the framework through absorption of a liquid.

33. The method for the regeneration of a bone of claim 29, wherein the framework is made of an elastomeric polymer and wherein the method further comprises fixing the framework into a compressed form prior to implantation and elastically expanding the framework through absorption of a liquid.

34. A granulate composed of at least two frameworks according to claim 1.

* * * * *

UNITED STATES PATENT AND TRADEMARK OFFICE
CERTIFICATE OF CORRECTION

| | |
|---|---|
| PATENT NO. | : 8,834,577 B2 |
| APPLICATION NO. | : 12/444367 |
| DATED | : September 16, 2014 |
| INVENTOR(S) | : Domonkos Horvath |

It is certified that error appears in the above-identified patent and that said Letters Patent is hereby corrected as shown below:

Title page item (73),

Assignee reads:   Celgen AG

Should read:   Celgen3D AG

Signed and Sealed this
Thirtieth Day of December, 2014

Michelle K. Lee
*Deputy Director of the United States Patent and Trademark Office*